(12) United States Patent
Hölscher et al.

(10) Patent No.: US 11,572,352 B2
(45) Date of Patent: Feb. 7, 2023

(54) METHOD FOR PRODUCING SCLAREOLIDE

(71) Applicant: SYMRISE AG, Holzminden (DE)

(72) Inventors: Bernd Hölscher, Halle (DE); Patrick Foley, New Haven, CT (US); Yonghua Yang, East Lyme, CT (US); Johannes Panten, Höxter (DE)

(73) Assignee: SYMRISE AG, Holzminden (DE)

( * ) Notice: Subject to any disclaimer, the term of this patent is extended or adjusted under 35 U.S.C. 154(b) by 106 days.

(21) Appl. No.: 17/269,729

(22) PCT Filed: Nov. 9, 2018

(86) PCT No.: PCT/EP2018/080743
§ 371 (c)(1),
(2) Date: Feb. 19, 2021

(87) PCT Pub. No.: WO2020/038592
PCT Pub. Date: Feb. 27, 2020

(65) Prior Publication Data
US 2021/0300885 A1 Sep. 30, 2021

Related U.S. Application Data

(60) Provisional application No. 62/721,732, filed on Aug. 23, 2018.

(51) Int. Cl.
C07D 307/92 (2006.01)

(52) U.S. Cl.
CPC ................... *C07D 307/92* (2013.01)

(58) Field of Classification Search
CPC ..................................... C07D 307/92
See application file for complete search history.

(56) References Cited

U.S. PATENT DOCUMENTS 8,252,565 B2 * 8/2012 Hama ................ C12P 7/22
435/155
2008/0319232 A1 12/2008 Nobis et al.

FOREIGN PATENT DOCUMENTS

SU 1409631 A1 7/1988

OTHER PUBLICATIONS

Barrero, A.F. et al., "Degration of the Side Chain of (-)-Sclareol: A Very Short Synthesis of nor-Ambreinolide and Ambrox", Synthetic Communicat, 2004, vol. 34, No. 19, pp. 3631-3643.
PCT/EP2018/080743; PCT International Search Report Written Opinion, dated Jan. 21, 2019, 11 pages.

* cited by examiner

*Primary Examiner* — Golam M Shameem
(74) *Attorney, Agent, or Firm* — Timothy H. Van Dyke; Wolter, Van Dyke, Davis, PLLC

(57) ABSTRACT

A method for producing slcareolide comprising the following steps: (a) providing sclareol as starter material; (b) contacting the starter material sclareol with ozone in air or oxygen as the sole oxidant in an acidic medium.

15 Claims, 2 Drawing Sheets

METHOD FOR PRODUCING SCLAREOLIDE

CROSS-REFERENCE TO RELATED APPLICATION

This application is a national stage entry of and claims priority to PCT/EP2018/080743, titled METHOD FOR PRODUCING SCLAREOLIDE, filed Nov. 9, 2018 which claims priority to U.S. Application No. 62/721,732 filed Aug. 23, 2018, which are hereby incorporated by reference in their entirety.

FIELD OF THE INVENTION

The present invention relates to a method for producing slcareolide.

STATE OF THE ART

Sclareolide is a sesquiterpene natural product that has found use in flavors and fragrances, both as an ingredient and as an intermediate. When used as an intermediate it is used primarily in the production of ambroxide, a highly sought after fragrance material possessing a powerful amber accord. While sclareolide is naturally occurring, commercially relevant quantities are generally prepared using a semi-synthetic approach starting with more readily available biological materials such as sclareol or abeniol (e.g. *Tetrahedron* 49 (45) p. 10405-10412, 1993).

In the case of using sclareol as a starting material, a well-studied cascade of oxidations can be used to convert the C20 diterpene olefin to the desired C15 sequiterpenene lactone. This conversion and its corresponding intermediates have been reported many times and a variety of conditions have been proposed (e.g., *Synthetic Communications* 31(5) p 749-758, 2001; *Synthetic Communications* 34(19) p. 3631-3643, 2004; *Synlett* 18 p. 2747-2750, 2010; *Helvetica Chimica Acta* 87 p. 2695, 2004). Common to all of the previously reported approaches is the use of multiple oxidants comprising Jones' Reagent, hydrogen peroxide, potassium permanganate, ozone, peracetic acid, sodium periodate, and manganese salts in various combinations of two or more. These efforts have resulted in the elucidation of multiple potential oxidation pathways, but all of them have drawbacks including the use of expensive reagents and multiple unit operations. Therefore it was the object of the present invention to convert slcareol to sclareolide using a single, cost-efficient oxidant.

DESCRIPTION OF THE INVENTION

This object is fully achieved by the subject matter of independent claim 1. Preferred embodiments of the present invention are subject matter of the dependent claims.

A first embodiment of the invention relates to a method for producing slcareolide comprising the following steps:
(a) providing sclareol as starter material;
(b) contacting the starter material sclareol with ozone in air or oxygen as the sole oxidant in an acidic medium.

Surprisingly, the inventors have found that under the correct conditions, ozone can be used as the sole oxidant for the multiple oxidation steps required to convert sclareol to sclareolide. Furthermore, this conversion according to the invention can be carried out in a single step. Therefore, the present invention can greatly reduce the cost of commercial production and can lead to an expanded use of sclareolide and its derivatives.

The formation of sclareolide from sclareol has been reported using various approaches with varying oxidation pathways. Perhaps the most common pathway, and the one that is most relevant to this invention, involves the cleavage of the sclareol (I) olefin, followed by a decarboxylation event to form a ketone (II). This ketone then undergoes an intramolecular condensation event to yield a cyclic enol-ether, often referred to as sclareoxide (III). Sclareoxide (III) can then be further oxidized to generate sclareolide (IV).

Figure 1:
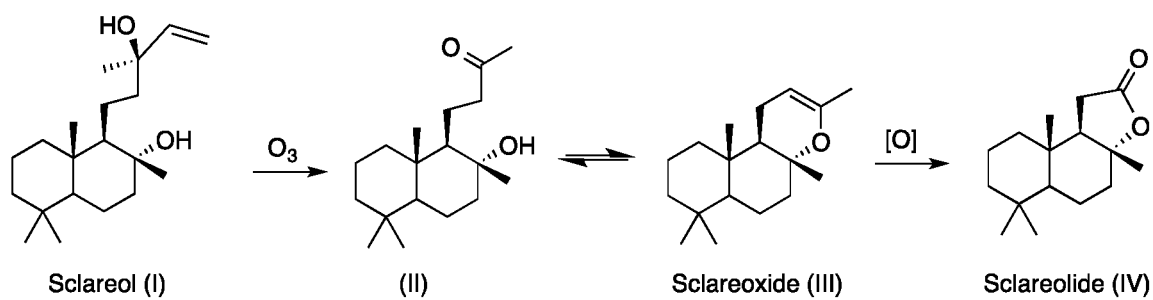
FIG. 1 provides a diagram showing a sequential oxidation of sclareol to generate sclareolide.
Figure 2:
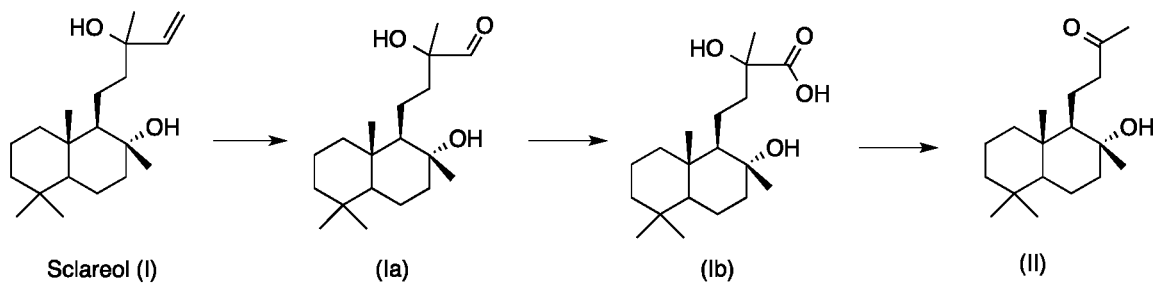
FIG. 2 provides a diagram showing a reaction involved in the conversion of (I) to (II) using ozone. The reaction involves the formation of an ozonide intermediate, which then fragments to give an aldehyde (Ia), which can be oxidized to a carboxylic acid (Ib). This acid can undergo a decarboxylation event to generate the desired ketone (II).

This sequence is shown in FIG. 1, which shows a sequential oxidation of sclareol to generate sclareolide Without wishing to be bound by theory, the conversion of (I) to (II) using ozone involves the formation of an ozonide intermediate, which then fragments to give an aldehyde (Ia), which can be oxidized to a carboxylic acid (Ib). This acid can undergo a decarboxylation event to generate the desired ketone (II), as it is shown in FIG. 2 (oxidative conversion of (I) to (II)). This degradation was further described in US 2008/0319232 A1.

Figure 3:
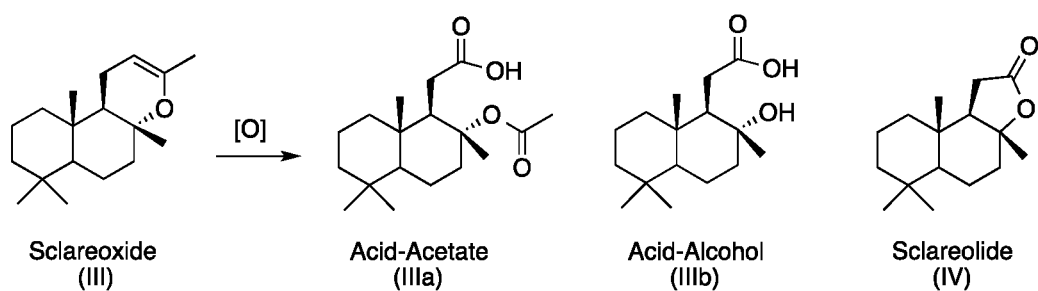
FIG. 3 provides a diagram which shows the oxidation of sclareoxide (III) to generate sclareolide and analogs.

The ketone (II) then cyclizes to generate sclareoxide (III), which can then be oxidized in a number of ways to cleave the olefin. Epoxidation using peracids followed by hydrolysis and diol cleavage has been commonly reported, as has heavy metal oxidation, but simple ozonolysis can also be used. The most common products resulting from the final oxidation in this sequence are the acid-acetate (IIIa), acid-alcohol (IIIb), and the desired sclareolide lactone (IV). This product mix is shown in FIG. 3, which shows the oxidation of sclareoxide (III) to generate sclareolide and analogs.

It is important to note that (IIIa) and (IIIb) can be easily converted to sclareolide (IV) through simple hydrolysis and ring closing. In this sense, (IIIa) and (IIIb) can be considered sclareolide analogs.

As previously mentioned, the full set of oxidations described in these pathways has previously been reported using multiple oxidants and unit operations. This invention, however, teaches that it can be done with ozone in oxygen and/or air as the sole oxidant under the correct conditions, i.e. in an acidic medium.

It was discovered that if in the presence of ozone a suitably acidic medium was used and optional a buffer such as, for example, sodium acetate, one could sequentially cleave slcareol's (I) olefin, oxidize the resulting aldehyde (Ia) to the acid (Ib), realize the decarboxylation event to give (II) and cyclization to (III), and then proceed through full cleavage of sclareoxide (III) to give mixtures of (IIIa), (IIIb), and sclareolide (IV). This surprising and unexpected result can be used to greatly improve the commercial production of sclareolide from sclareol.

The importance of the solvent system for this transformation is critical. To highlight this, it was observed that if a simple, non-acidic solvent was used, the major product after several hours of reaction was simply the first cleavage product (Ia), indicating that the subsequent oxidations were not taking place. However if an appropriate acid is present, then the reaction proceeds directly through to the next steps in the cascade. Further, the presence of acid is critically important in the cyclization and dehydration of the ketone (II) intermediate, for if this did not readily take place the reaction progress would again become so slow as to be commercially unfeasible.

While ozone in air and/or oxygen are the sole oxidants that are added to the system, there may be many intermediary oxidation species that form that may participate in the cascade of reactions. These important species may be singlet oxygen, hydrogen peroxide, ozonide, acyl radical, peracid, and/or any other oxygen species. These reagents, should they form, need not be added separately, however.

In one embodiment according to the invention the aidic media comprises organic acids. Preferred acids include acetic acid, propanoic acid, and any C2-C18 saturated alkyl acid. For example, acids such as hydrochloric acid, sulfuric acid, tosyl acid, mesyl acid, phosphoric acid, and formic acid can also be used. Any of these acids can be used in combination with a traditional organic solvent or with water. Buffers can also be used, including sodium acetate, sodium hydroxide, phosphates, citric acid, or borates, just to name a few.

In a preferred embodiment according to the invention the organic acid is selected from the group consisting of formic acid, oxalic acid, propanoic acid, butyric acid, pentanoic acid, hexanoic acid, heptanoic acid, octanoic acid, nonanoic acid, decanoic acid, undecanoic acid, dodceanoic acid, tridecanoic acid, palmitic acid, pentadecanoic acid, stearic acid, acetic acid and/or any isomers or diacids thereof. In a most preferred embodiment according to the invention the organic acid is acetic acid.

In a further embodiment according to the invention the acidic medium further comprises an organic solvent or water. In a most preferred embodiment according to the invention the acidic medium comprises acetic acid and water.

In one embodiment according to the invention the acidic medium is buffered to a pH between pH 1 and pH 6. In a preferred embodiment according to the invention the acidic medium is buffered to a pH between pH 2 and pH 4.

Inorganic oxidation catalysts may also be included in the reaction mixture to accelerate the reaction rate, but are not required. Metal oxides such as, for example, MnO, $V_2O_5$, $MoO_3$, and $WO_3$ would be suitable, as well as, for example, Fe, Ni, and/or Cu catalysts.

In one embodiment according to the invention the acidic medium further comprises one or more inorganic acids selected from the group consisting of $BF_3$, HCl, $H_2SO_4$, $H_3PO_4$, or $HNO_3$, or $B(OH)_3$. In a further embodiment according to the invention the acidic medium may further comprise methanesulfonic acid, toluenesulfonic acid, trifluoroacetic acid, trichloroacetic acid and/or acidic resin.

The reaction can be carried out at wide range of temperatures, from cryogenic to heated. The reaction, however, proceeds nicely at temperatures ranging from 0-40° C., and indeed can be carried out at room temperature with provisions for cooling as it is an exothermic reaction. In a preferred embodiment according to the invention the reaction is been carried out at room temperature. In another preferred embodiment according to the invention the reaction temperature does not exceed 30° C.

The conversion can further be carried out in any manner of reactor suitable for handling ozone. These reactors can be batch, semi-continuous, or fully continuous. In a preferred embodiment, the reactor would be a continuous falling film reactor.

In another embodiment according to the invention the ozone in air or oxygen is contacted with the acidic medium trough sparging. In a further embodiment according to the invention the ozone in air or oxygen is contacted with the acidic medium through diffusion of gas into a film.

Furthermore, it might be advantageous that the ozone in air or oxygen is contacted with the acidic medium in intervals.

In a further embodiment according to the invention the air in which the ozone is present, is enriched with nitrogen. This is advantageous, because, for example, the presence of impurities, for example radicals, can be avoided.

Ozone concentrations can range from 0.1 to 15% $O_3$ in $O_2$ by weight, but can be more preferably kept in the range of 1-10% by weight. In a preferred embodiment according to the invention the ozone concentration is in the range of 3-10% by weight. The flow rates of the oxygen gas into the system can very widely, and depends on the gas-liquid contacting mechanism. Regardless of the flow rate or contacting mechanism, it is preferred to use at least 2 molar equivalents of ozone with respect to sclareol for the reaction to proceed to completion. Further molar excess can easily be used as well.

Figure 4:
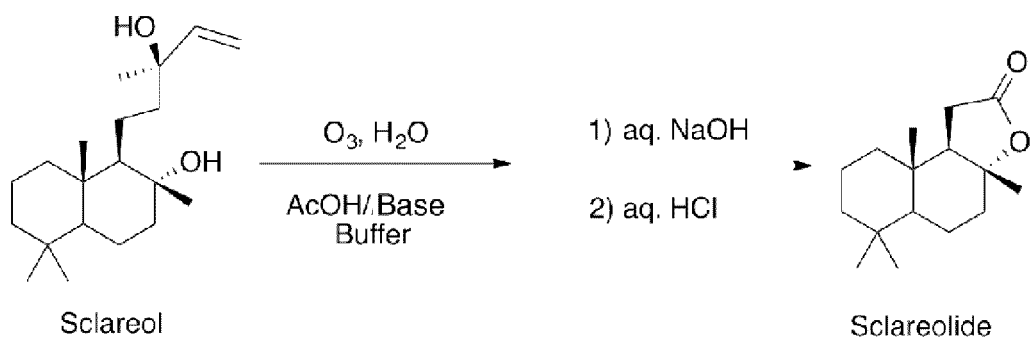
FIG. 4 provides a diagram showing a reaction for the preparation of sclareolide.

Example 1—Buffered Aqueous Acetic Acid with Work-Up to Convert Sclareolide Analogs The preparation of Sclareolide is shown in FIG. 4.

Sclareol (100 g) is dissolved in acetic acid (240 g) and is then combined with water (152 g) and sodium hydroxide (8 g). The solution is stirred at 20° C. and a 10% by weight stream of $O_3$ in $O_2$ is passed through the mixture at 3.0 lpm for 5 hrs with cooling to ensure the reaction temperature does not exceed 30° C. At the end of 5 hrs, the solution is purged with nitrogen gas. To quench peroxide, sodium sulfite (5.5 g) is added and after several minutes the pH is adjusted to pH 2 with 6 M HCl. The mixture is then extracted with a mixture of ethyl acetate:heptane, 1:2, (2×300 ml). The combined organics are then washed with a 2:1, Water:Brine mixture (2×150 ml), dried with Sodium Sulfate, filtered, and concentrated to give 87-89 g of thick, light yellow translucent solid.

This material is then dissolved in 250 ml tetrahydrofuran (THF) and is charged with 295 ml of 10% NaOH (aq). This material is then stirred at 55° C. overnight. The following morning the solution is acidified to pH 1 with 140 ml of 6 M HCl and stirring is continued for several hours until TLC reveals full conversion to cyclized product. The pH of this material is then adjusted to pH 4 and THF is removed under vacuum. The aqueous phase is then extracted with Heptane (2×250 ml). The combined organics are then washed with a 2:1, Water:Brine mixture (2×150 ml), dried with sodium sulfate, filtered, and are concentrated to give 78-80 g of amorphous solid, which is 95-96% of the theoretical mass balance.

Example 2—Buffered Aqueous Acetic Acid with Alternative Work-Up to Convert Sclareolide Analogs Sclareol (100 g) was dissolved in acetic acid (240 g) and was then combined with water (152 g) and sodium hydroxide (4 g). The solution was stirred at 20° C. and a 10% by weight stream of $O_3$ in $O_2$ was passed through the mixture at 3.0 lpm for 4 hrs with cooling to ensure the reaction temperature did not exceed 30° C. At the end of 4 hrs, the solution is purged with nitrogen. The pH of the mixture was ~4. 1.5 L of water was added to the mixture, white solid formed over night at room temperature. The white solid was collected and treated with NaOH/H$_2$O (51.8 g/0.75 L) at 50° C. for 3 hours, until TLC showed the deacetylation was completed. The reaction was then cooled to RT, and acidified to pH 2-3 with HCl (2N). The mixture was extracted with toluene three times (500 mL+300 mL+200 mL), and the combined toluene fractions are refluxed at 110-130° C. for 5-7 hours with a Dean-Stark unit to remove all the water formed during the ring-closing process. The toluene is evaporated and the residue is dissolved into an ethanol/water mixture (400 mL/150 mL). This mixture is then poured into a crystallization plate and the liquid is allowed to evaporate. White-yellow dry solid (78.0 g) is obtained after drying over the weekend at room temperature. QA-NMR shows the purity is 65.2%.

The invention claimed is:

1. A method for producing slcareolide comprising the following steps:
   (a) providing sclareol as starter material;
   (b) contacting the starter material sclareol with ozone in air or oxygen as the sole oxidant in an acidic medium.

2. The method according to claim 1, wherein the acidic medium comprises one or more organic acids.

3. The method according to claim 2, wherein the organic acids are selected from the group consisting of formic acid, oxalic acid, propanoic acid, butyric acid, pentanoic acid, hexanoic acid, heptanoic acid, octanoic acid, nonanoic acid, decanoic acid, undecanoic acid, dodceanoic acid, tridecanoic acid, palmitic acid, pentadecanoic acid, stearic acid, acetic acid and/or any isomers or diacids thereof.

4. The method according to claim 1, wherein the acidic medium further comprises an organic solvent or water.

5. The method according to claim 1, wherein the acidic medium comprises acetic acid and water.

6. The method according to claim 1, wherein the acidic medium is buffered to a pH between pH 1 and pH 6.

7. The method according to claim 5, wherein the acidic medium is buffered to a pH between pH 2 and pH 4.

8. The method according claim 1, wherein the acidic medium comprises one or more inorganic acids selected from the group consisting of BF$_3$, HCl, H$_2$SO$_4$, H$_3$PO$_4$, or HNO$_3$, or B(OH)$_3$.

9. The method according to claim 1, wherein the acidic medium further comprises methanesulfonic acid, toluenesulfonic acid, trifluoroacetic acid, trichloroacetic acid and/or acidic resin.

10. The method according to claim 1, wherein the reaction is carried out between 0 and 40° C.

11. The method according to claim 1, wherein the ozone in air or oxygen is contacted with the acidic medium through sparging.

12. The method according to claim 1, wherein the ozone in air or oxygen is contacted with the acidic medium through diffusion of gas into a film.

13. The method according to claim 12, wherein the ozone in air or oxygen is contacted with the acidic medium in intervals.

14. The method according to claim 1, wherein the ozone concentration in oxygen is in the range of between 0.1 and 15% by weight.

15. The method according to claim 1, wherein the ozone is present in air and wherein the air is enriched with nitrogen.

* * * * *